(12) United States Patent
Tanji et al.

(10) Patent No.: US 8,611,179 B2
(45) Date of Patent: Dec. 17, 2013

(54) ACOUSTIC WAVE MEASURING SYSTEM AND METHOD OF GENERATING IMAGE DATA THEREOF

(75) Inventors: Koichi Tanji, Kawasaki (JP); Katsuhiro Watanabe, Wako (JP); Yasufumi Asao, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 396 days.

(21) Appl. No.: 13/009,699

(22) Filed: Jan. 19, 2011

(65) Prior Publication Data

US 2011/0182136 A1 Jul. 28, 2011

(30) Foreign Application Priority Data

Jan. 22, 2010 (JP) ................................ 2010-012192

(51) Int. Cl.
G03B 42/06 (2006.01)
A61B 8/00 (2006.01)
A61B 5/05 (2006.01)

(52) U.S. Cl.
USPC ............................... 367/7; 600/443; 600/425

(58) Field of Classification Search
USPC .................................................. 367/7; 73/655
See application file for complete search history.

(56) References Cited

U.S. PATENT DOCUMENTS

| | | | | |
|---|---|---|---|---|
| 4,611,494 A * | 9/1986 | Uchiyama | | 73/626 |
| 4,662,223 A * | 5/1987 | Riley et al. | | 73/626 |
| 4,835,689 A | 5/1989 | O'Donnell | | |
| 6,607,489 B2 | 8/2003 | Hoctor et al. | | |
| 7,693,006 B2 * | 4/2010 | Lou et al. | | 367/57 |
| 7,756,246 B2 * | 7/2010 | Mikami et al. | | 378/37 |
| 2002/0173722 A1 * | 11/2002 | Hoctor et al. | | 600/443 |
| 2008/0106974 A1 * | 5/2008 | Bergery | | 367/38 |
| 2009/0066949 A1 * | 3/2009 | Masumura | | 356/326 |
| 2009/0069674 A1 * | 3/2009 | Masumura et al. | | 600/425 |
| 2010/0118653 A1 * | 5/2010 | He et al. | | 367/57 |

FOREIGN PATENT DOCUMENTS

WO 2001/026555 A1 4/2001

OTHER PUBLICATIONS

Berkhoff et al., "Ultrasound Wave Propagation Through Rough Interfaces: Iterative Methods", Journal of Acoustic Society of America, Mar. 1996, pp. 1306-1314, vol. 99, No. 3.

Xu et al., "Photoacoustic Imaging in Biomedicine", Review of Scientific Instruments, Apr. 2006, pp. 041101-1-041101-22, vol. 77.

* cited by examiner

*Primary Examiner* — Isam Alsomiri
*Assistant Examiner* — Hovhannes Baghdasaryan
(74) *Attorney, Agent, or Firm* — Canon USA Inc. IP Division

(57) ABSTRACT

When correcting the acoustic wave refraction occurring on the interface between mediums having different sound speeds by Snell's law, an applicable back-projection method is limited to a time domain method. An image data generating method performed to receive and convert an acoustic wave generated by irradiating a subject with light into a first electrical signal with an acoustic wave receiver via a medium having a sound speed different from that of the subject, and to generate image data based on the first electrical signal is provided, wherein a second electrical signal obtained when the acoustic wave is received at each virtual reception point is generated based on the first electrical signal through an integral calculation performed by using an advanced Green's function, and image data is generated based on the second electrical signal.

20 Claims, 10 Drawing Sheets

FIG. 8
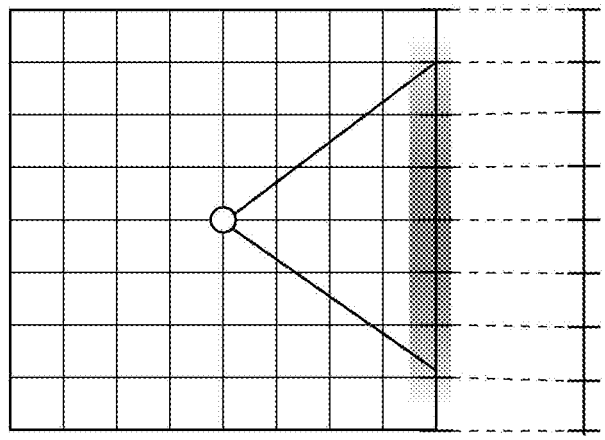
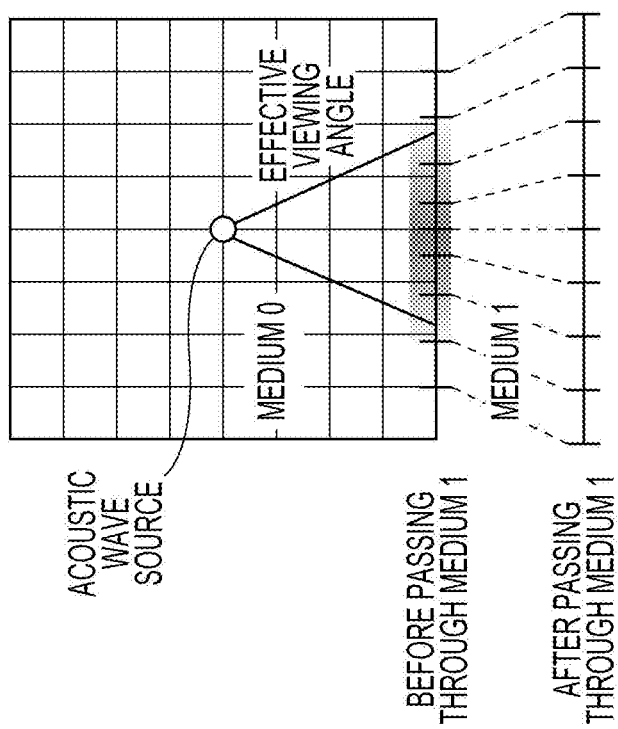

ACOUSTIC WAVE MEASURING SYSTEM AND METHOD OF GENERATING IMAGE DATA THEREOF

BACKGROUND OF THE INVENTION

1. Field of the Invention

The present invention relates to an acoustic wave measuring system configured to receive an acoustic wave and generate image signals thereof; the present invention also relates to a method of generating image date based on the image signals generated by the measuring system.

2. Description of the Related Art

In recent years, photoacoustic tomography (PAT) devices have received increasing interest due to the remarkable advantages of PAT. In PAT, a subject is irradiated with pulsed light emitted from a light source such as a laser. The pulsed light is propagated through the subject, and an acoustic wave (e.g., an ultrasonic wave) is generated when the pulse light propagating through the subject is absorbed by a target for measurement located within the subject. The acoustic wave is received and measured by an acoustic wave receiver (transducer) placed around the subject. Then, the distribution of initially generated pressures and/or that of absorption coefficients observed within the subject is changed into image data (imaging) based on an electrical signal output from the acoustic wave receiver.

As a method of generating image data of a light absorber provided in the subject (performing the image reconstruction), there are known methods of generating image data by back-projecting a measured signal, including a time domain method, a Fourier domain method, etc. Taking a system for making a diagnosis of human body as an example, the sound speeds of parts (mediums) of the structure of the system may be different from each other. For example, when the acoustic wave receiver is provided on one side of a human body, and the subject is fixed and held with a compression plate, the sound speed of the subject may be different from that of the compression plate. Indeed, different tissue parts including a fat layer, a muscle layer or the like that are included in the subject have different sound speeds. In addition, acoustic wave refraction occurs on each interface between the above-described compression plate and the different tissue parts having different sound speeds. The acoustic wave refraction coupled with the different sound speeds causes image degradation. Therefore, a method of correcting the effect of the acoustic wave refraction occurring on the interface between the mediums (e.g., an interface between the compression plate and the subject) by applying Snell's law, and generating image data according to the time domain method has been proposed in U.S. Pat. No. 6,607,489.

However, according to the method of correcting the acoustic wave refraction by Snell's law, which is exemplarily disclosed in U.S. Pat. No. 6,607,489, points that are provided after the acoustic wave refraction is corrected are not provided at regular intervals. More specifically, the points are provided before the acoustic wave passes through the compression plate, and a signal $s_0(x_0, t_0)$ (illustrated in FIG. 7B herein) is obtained at each of the points. Hereinafter, each of the above-described points is referred to as a "virtual reception point". Accordingly, an applicable back-projection method is limited only to the time domain method. Further, when the above-described refraction correction is applied for the time domain method, the virtual reception points are not provided at regular intervals, and an effective viewing angle is reduced because the distribution of the virtual reception points is tilted.

SUMMARY OF THE INVENTION

At least one embodiment of the present invention is directed to an acoustic wave measuring system and a method for generating image data thereof that can be applied not only for the time domain method, but also to the Fourier domain method while reducing the effect of the acoustic wave refraction occurring on the interface between mediums having different sound speeds (e.g., the subject and the compression plate).

One aspect of the present invention is directed to an image data generating method performed to receive and convert an acoustic wave generated by irradiating a subject with light into a first electrical signal with an acoustic wave receiver via a medium having a sound speed different from a sound speed of the subject, and to generate image data based on the first electrical signal, the method includes the steps of generating a second electrical signal obtained when the acoustic wave is received at each of virtual reception points that are set on an interface between the subject and the medium and/or a side beyond the interface, the side corresponding to the subject, based on the first electrical signal through an integral calculation performed by using an advanced Green's function, and generating image data based on the second electrical signal.

Another aspect of the present invention is directed to an acoustic wave measuring system including an acoustic wave receiver provided to receive and convert an acoustic wave generated by irradiating a subject with light into a first electrical signal, a medium having a sound speed different from a sound speed of the subject, the medium being provided between the subject and the acoustic wave receiver, and a signal processing device generating image data based on the first electrical signal, wherein the signal processing device generates a second electrical signal obtained when the acoustic wave is received at each of virtual reception points that are set on an interface between the subject and the medium and/or a side beyond the interface, the side corresponding to the subject, based on the first electrical signal through an integral calculation performed by using an advanced Green's function, and generates image data based on the second electrical signal.

The present invention provides a general-purpose image data generating method and a general-purpose acoustic wave measuring system that can be applied not only for the time domain method, but Fourier domain method while reducing the effect of the acoustic wave refraction occurring on the interface between mediums having different sound speeds by considering an electrical signal obtained when an acoustic wave is received at a virtual reception point.

Further features of the present invention will become apparent from the following description of exemplary embodiments with reference to the attached drawings.

BRIEF DESCRIPTION OF THE DRAWINGS

FIG. 8 schematically illustrates the difference between an effective viewing angle obtained according to a known method and an effective viewing angle obtained according to an embodiment of the present invention.

DESCRIPTION OF THE EMBODIMENTS

Next, embodiments of the present invention will be specifically described with reference to the attached flowcharts and drawings. It should be noted that the present invention may be achieved without being limited to the above-described embodiments. In the present invention, an acoustic wave includes a sonic wave, an ultrasonic wave, and a photoacoustic wave, and indicates an elastic wave generated within a subject when the subject is irradiated with light (an electromagnetic wave) such as a near infrared radiation.

Figure 1:
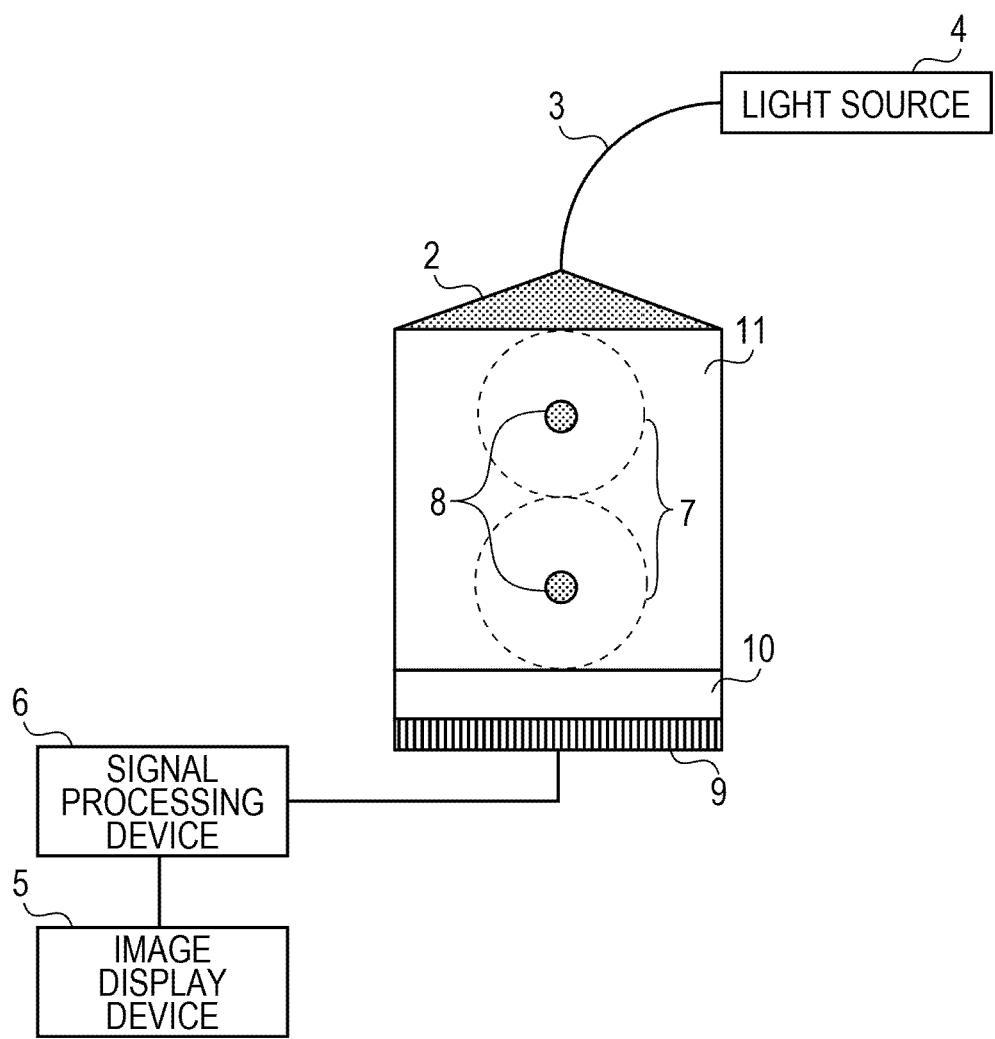
FIG. 1 schematically illustrates an exemplary configuration of an acoustic wave measuring system according to an embodiment of the present invention.

First, an exemplary configuration of an acoustic wave measuring system according to an embodiment of the present invention will be described with reference to FIG. 1. The acoustic wave measuring system includes a light source 4 provided to irradiate a living body which is a subject 11 with pulsed light 2. Usually, the surface of the subject is irradiated with the pulsed light 2 generated from the light source 4 via a light-propagation device 3 including an optical fiber, a liquid light guide, or the like. However, the light-propagation device 3 may be omitted, and the pulsed light 2 may reach the subject via free space by using optical elements, such as a lens, a mirror, etc. Upon reaching the subject, the pulsed light propagates within the subject and generates an acoustic wave 7 from a target region thereof. The acoustic wave measuring system also includes an acoustic wave receiver 9 arranged in the vicinity of the subject to receive and convert an acoustic wave 7 into an electric signal. The acoustic wave 7 is generated with a light absorber 8 absorbing part of the energy of the light, where the light absorber 8 is provided in the subject. The acoustic wave receiver 9 includes a plurality of acoustic wave-reception elements, where each of the elements receives and converts the acoustic wave 7 into an electrical signal (first electric signal). The acoustic wave-reception elements are arranged in a one-dimensional array or a two-dimensional matrix. A compression plate 10 which is a subject-fixing member provided to fix the form of at least part of the subject is disposed in front of the acoustic wave receiver 9. That is, the compression plate 10 is located in the space between the acoustic wave receiver 9 and the subject 11. The acoustic wave measuring system further includes a signal processing device 6 provided to analyze the electrical signal obtained with the acoustic wave receiver 9 and to generate image data based on the electric signal. After amplifying and performing A/D conversion for the electrical signal obtained with the acoustic wave receiver 9, the signal processing device 6 performs the image reconstruction based on a digital electrical signal and acquires information about the value of optical characteristics that are observed inside the subject as the image data. The optical characteristic value information indicates the distribution of generation sources of an acoustic wave generated through light irradiation, the distribution of initial sound pressures occurring inside the subject, the optical energy absorption-density distribution derived from the initial sound pressure distribution, the absorption coefficient distribution, and the distribution of information about the density of a substance included in the tissue. The substance density information distribution indicates, for example, the oxygen saturation distribution, the oxy/reduced hemoglobin density, etc. As the characteristic processing of an embodiment of the present invention, image data less affected by the acoustic wave refraction occurring on the interface between mediums having different sound speeds is generated through an integration performed by using an advanced Green's function. The details of the image data generation will be described later with reference to FIG. 4 and others. The signal processing device 6 includes an electrical signal processing unit including an amplifier, an A/D converter, a field programmable gate array (FPGA) chip, etc., and an image reconstruction unit such as a work station.

An image display device 5, such as an LCD or LED display device, is provided to display an image generated based on the image data. In the present invention, the term "image data" indicates information about the inside of the subject, which is shown as either one of a two-dimensional image and a three-dimensional image. A back-projection method is a way for generating the image data, that is, a way for performing the image reconstruction.

Figure 3:
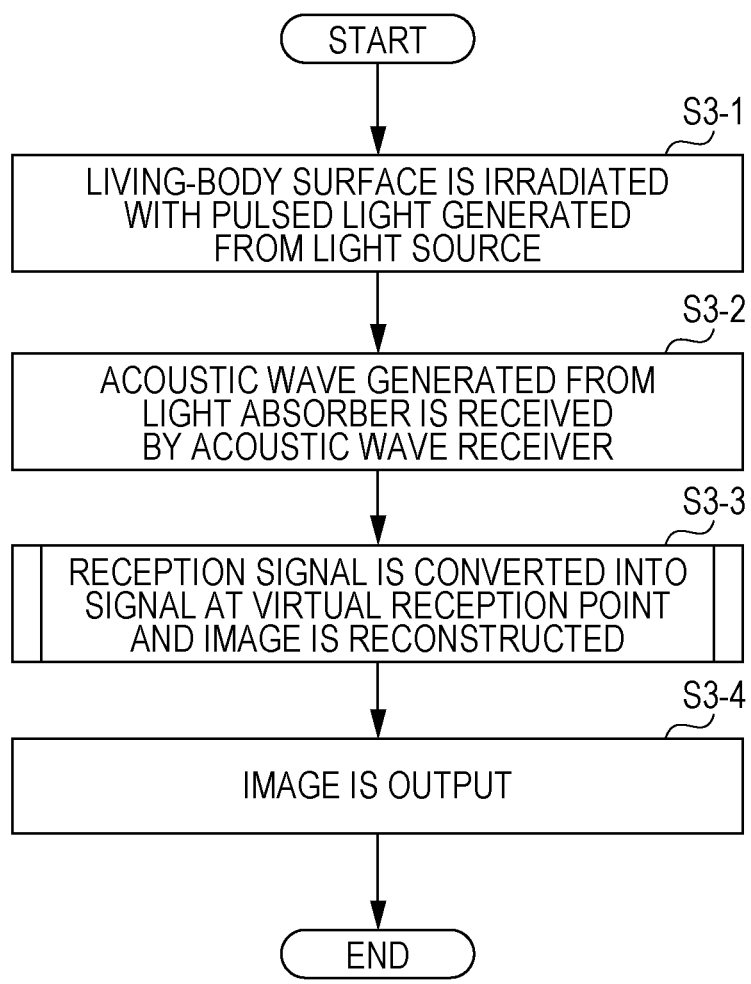
FIG. 3 is an exemplary flowchart illustrating process steps to obtain information about the distribution of optical characteristics that are observed within a living body with an acoustic wave measuring system according to an embodiment of the present invention.

FIG. 3 is a flowchart illustrating the processes of irradiating the subject with light, generating the image data, and outputting data of a result of the image generation according to an embodiment of the present invention. The flowchart will be described, along with the configurations that are illustrated in FIG. 1.

First, the surface of the subject 11 is irradiated with the pulsed light 2 generated from the light source 4 at step S3-1. Since the speed of the pulsed light 2 is high, the time when the light source 4 generates the pulsed light 2 is considered to be substantially the same as the time when the subject is irradiated with the pulsed light 2.

Figure 2:
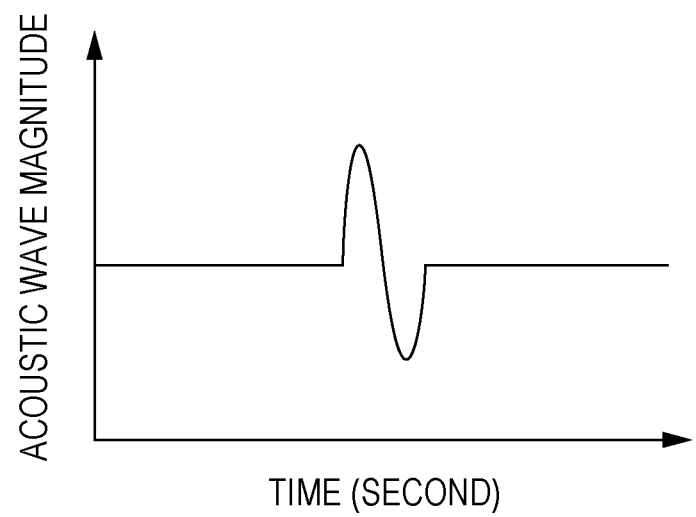
FIG. 2 schematically illustrates an exemplary reception signal output from an acoustic wave measuring system according to an embodiment of the present invention.

At step S3-2, an acoustic wave generated from the light absorber 8 provided in the subject is received and converted into an electrical signal (hereinafter referred to as a "reception signal") with the acoustic wave receiver 9. Usually, the reception signal of the acoustic wave generated from the light absorber 8 which is a spherical object shows an N-shaped waveform illustrated in FIG. 2, where the time is shown on the horizontal axis and the magnitude of the acoustic wave is shown on the vertical axis.

At step S3-3, the reception signal obtained at step S3-2 is converted into an electrical signal obtained when the acoustic wave is received on a virtual reception point according to a method that will be described later (hereinafter referred to as a "virtual reception signal") and the image reconstruction is performed based on the virtual reception signal. That is, the acoustic wave refraction occurring on the interface between the subject 11 and the compression plate 10 is corrected and the image data is generated at step S3-3.

Then, at step S3-4, an image is output based on the generated image data, and the image is displayed with the image display device 5.

Next, a method of correcting the refraction of an acoustic wave (a method of generating the virtual reception signal) according to an embodiment of the present invention will be described. Hereinafter, the refraction-correction method will be described based on the premise that a two-dimensional image is displayed for the sake of simplicity. The principle of the method remains the same even though a three-dimensional image is displayed.

An embodiment of the present invention is achieved by calculating time evolution through the integration performed by using the advanced Green's function. The time evolution is opposite in direction to ordinary time evolution (corresponding to an integration performed by using a retarded Green's function). That is, performing an integration by using the advanced Green's function while determining a reception signal obtained after the acoustic wave passes through a given medium (e.g., the compression plate) to be a source allows for calculating a virtual reception signal obtained at a point arbitrarily specified before the acoustic wave passes through the given medium (hereinafter referred to as a virtual reception point). That is, the use of the advanced Green's function allows for converting a reception signal into a virtual reception signal.

Figure 4:
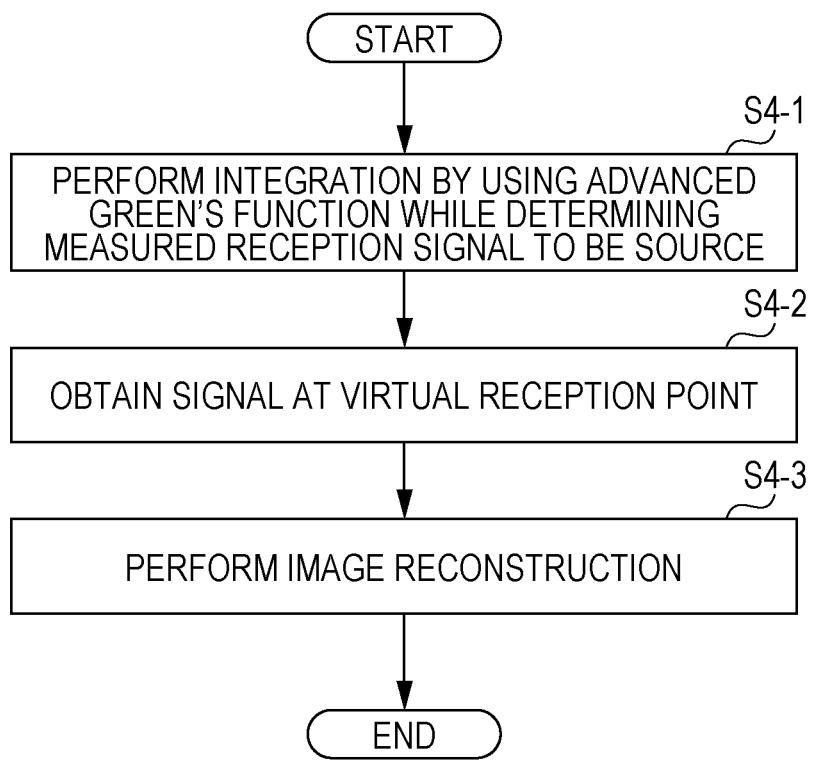
FIG. 4 is a flowchart illustrating processing steps that are performed with a signal processing device according to an embodiment of the present invention.
Figure 5:
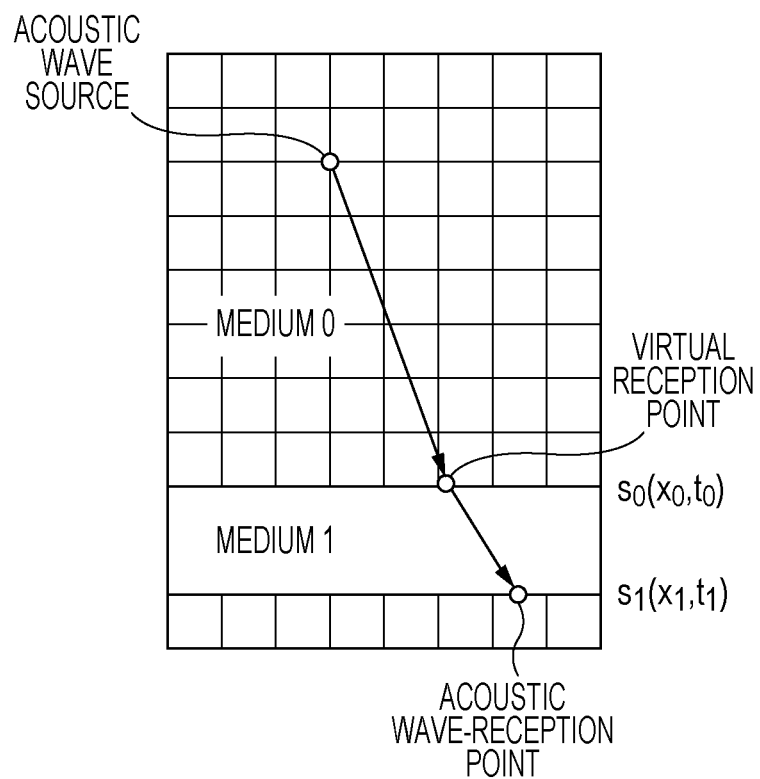
FIG. 5 schematically illustrates the acoustic wave refraction occurring on the interface between mediums having different sound speeds.

FIG. 4 is an exemplary flowchart illustrating an image data generating method performed with the signal processing device 6 according to an embodiment of the present invention. FIG. 5 schematically illustrates a medium 0 (e.g., the subject) and a medium 1 (e.g., the compression plate) that are provided as mediums having different sound speeds, and the relationship between a signal $s_0(x_0, t_0)$ which is a virtual reception signal obtained before the acoustic wave passes through the medium 1 and a signal $s_1(x_1, t_1)$ which is a signal obtained after the acoustic wave passes through the medium 1, where the signal $s_1(x_1, t_1)$ is a reception signal which is actually output from the acoustic wave receiver 9. The sound speed measured within the medium 0 is determined to be $c_0$ and that measured within the medium 1 is determined to be $c_1$. Here, the signal $s_0(x_0, t_0)$ is a virtual reception signal obtained at coordinates $(x_0, t_0)$, and the signal $s_1(x_1, t_1)$ is a reception signal obtained at coordinates $(x_1, t_1)$ (a signal including all of reception signals that are output from at least two elements corresponding to at least two acoustic wave-reception points, which are received at coordinates $(x_1, t_1)$).

Hereinafter, processing procedures will be described based on the flowchart illustrated in FIG. 4.

At step S4-1, a reception signal output when the acoustic wave receiver 9 actually receives the acoustic wave is determined to be a source, and an integration is performed by using the advanced Green's function according to Equation (1). The above-described processing allows for obtaining the signal $s_0(x_0, t_0)$ obtained before the acoustic wave passes through the medium 1 based on the signal $s_1 (x_1, t_1)$ obtained after the acoustic wave passes through the medium 1. Here, the variable x indicates a positional coordinate and the variable t indicates time. An advanced Green's function $G_A$ is provided based on a retarded Green's function illustrated in Equation (4) corresponding to a wave equation which is a primitive equation of the acoustic wave propagation, the wave equation being illustrated in Equation (3), and the relationship between the advanced Green's function $G_A$ and a retarded Green's function $G_R$, which is illustrated in Equation (2). Here, the star sign "*" shown on the right side of Equation (2) indicates a complex conjugate.

$$s_0(x_0, t_0) = \int G_A(x_1 - x_0, t_1 - t_0) s_1(x_1, t_1) dx_1 dt_1 \quad \text{Equation (1)}$$

$$G_A(x - x', t - t') = G_R^*(x' - x, t' - t) \quad \text{Equation (2)}$$

$$\nabla^2 p(x, y, t) - \frac{1}{c_1^2} \frac{\partial^2}{\partial t^2} p(x, y, t) = 0 \quad \text{Equation (3)}$$

$$G_R(x_1 - x_0, t_1 - t_0) = \frac{\delta\left(t_1 - t_0 - \frac{|x_1 - x_0|}{c_1}\right)}{4\pi |x_1 - x_0|} \quad \text{Equation (4)}$$

At step S4-2, a virtual signal received at the virtual reception point is obtained with the above-described integral calculation. Since the signal $s_0(x_0, t_0)$ is obtained through the integral calculation performed at step S4-1, steps S4-1 and S4-2 are illustrated as separate steps in FIG. 4. However, it may be considered that steps S4-1 and S4-2 are actually the same step.

At step S4-3, the image reconstruction is performed based on the virtual signals that are received at the virtual reception points. The back-projection method (including the time domain method, the Fourier domain method, etc.) may be used as a method of performing the image reconstruction. As for the time domain method and the Fourier domain method, please see "Photoacoustic imaging in biomedicine" REVIEW OF SCIENTIFIC INSTRUMENTS 77, 041101 (2006).

Figure 6:
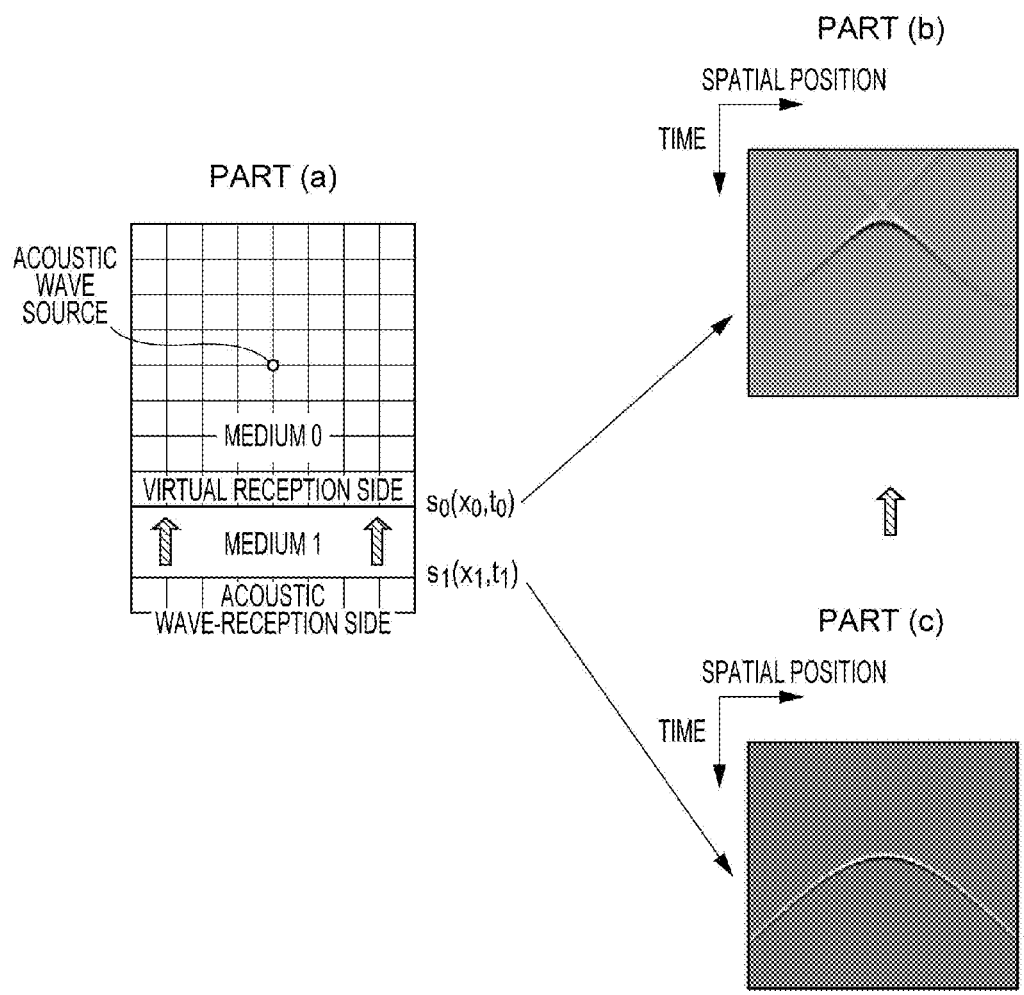
FIG. 6 schematically illustrates the relationship between a reception signal output from an acoustic wave receiver and a reception signal obtained at a virtual reception point obtained through mapping of the reception signal output from the acoustic wave receiver.

FIG. 6 illustrates the signal $s_0(x_0, t_0)$ obtained at the virtual reception point before the acoustic wave passes through the medium 1 (see part (b) of FIG. 6) based on the signal $s_1(x_1, t_1)$ obtained after the acoustic wave passes through the medium 1 (see part (c) of FIG. 6) according to the present method in the case where the acoustic wave source (the light absorber 8) is considered to be a point (see part (a) of FIG. 6). Here, the horizontal axis illustrated in each of parts (b) and (c) of FIG. 6 indicates the spatial position corresponding to the reception point of the acoustic wave, and the vertical axis illustrated in each of parts (b) and (c) of FIG. 6 indicates the time when the signal sampling is performed. Since the sound speed measured within the medium 0 (the subject area) before the acoustic wave passes through the medium 1 is constant, considering the signal $s_0(x_0, t_0)$ allows for performing the image reconstruction according to the back-projection method by determining the virtual reception point to be the start point. The above-described method allows for reducing the degradation of an image (image data), which is caused by the refraction of the acoustic wave.

Figure 7A:
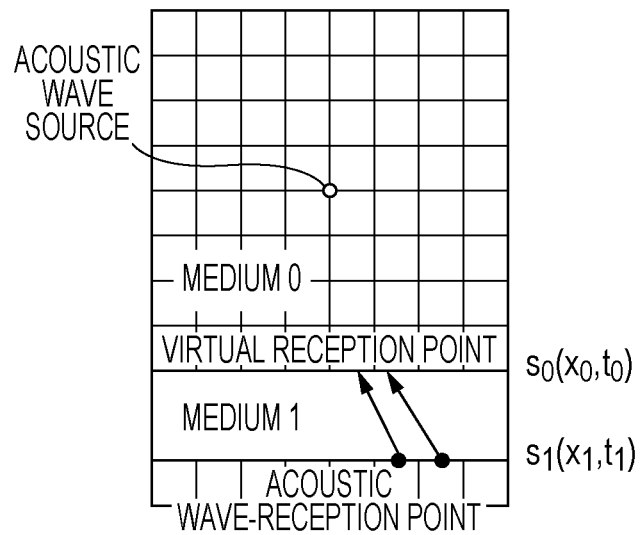
FIG. 7A is a schematic diagram illustrating the relationship between a reception point and a virtual reception point that are obtained according to a known method.
Figure 7B:
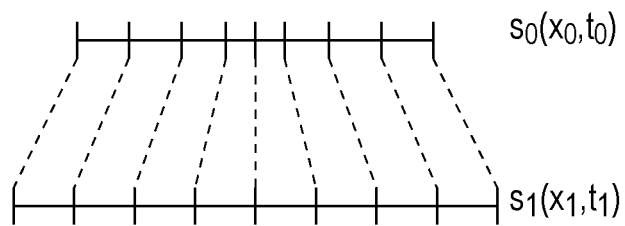
FIG. 7B is another schematic diagram illustrating the relationship between the reception point and the virtual reception point that are obtained according to the known method.

Each of FIGS. 7A and 7B schematically illustrates a known refraction correction method performed by Snell's law. According to the known method, the virtual reception point of the acoustic wave is obtained by Snell's law based on the reception point of the acoustic wave (see FIG. 7A).

Therefore, when the sound speeds of the mediums 0 and 1 are different from each other and actual reception points of the acoustic wave are regularly spaced, the virtual reception points of the acoustic wave are not regularly spaced (see FIG. 7B). However, when the Fourier domain method is applied as the image reconstruction method, there should be a linear relationship between a time frequency and a space frequency due to dispersion relation of the acoustic wave. Therefore, when time sampling is performed at regular intervals at the acoustic-wave acquisition time, the reception points corresponding to the space frequency should be provided at regular intervals. Therefore, when the known refraction correction method is performed as it is, it is difficult to apply the Fourier domain method, which is performed based on the premise that the reception points of the acoustic wave are spaced at regular intervals. Here, interpolation allows for obtaining signals that are provided on regularly spaced points based on signals that are provided on irregularly spaced points. However, when reception points are widely spaced, the image resolution is reduced due to information dissipation caused by the interpolation. Therefore, the interpolation is not desirable.

On the other hand, an embodiment of the present invention allows for setting a virtual reception point at an arbitrary position and obtaining a virtual reception signal at the virtual reception point.

Therefore, it becomes possible to obtain virtual reception signals on regularly-spaced points from the start, which is adequate for performing the Fourier domain method. Further, when applying fast Fourier transformation (FFT) used for the Fourier domain method, the number of signal points targeted for processing should be a power of two. Although the number of reception points is not a power of two, therefore, an embodiment of the present invention allows for generating signals on power-of-two virtual reception points to achieve the application of FFT.

Further, an embodiment of the present invention can be applied for the time domain method. When the refraction correction is performed according to the time domain method, virtual reception signals are obtained on regularly-spaced virtual reception points, and the weight of distribution of the virtual reception points is not given to an effective viewing angle unlike the case where the known refraction correction method performed by Snell's law is applied. Consequently, the effective viewing angle is not reduced. Here, the reduction in the effective viewing angle denotes a reduction in an effectual viewing angle, which is caused by points where signals exist, the points being tilted toward the center due to the weighting. FIG. 8 illustrates a change in the effective viewing angle, which is observed in each of the case where the known method is applied for the refraction correction (part (a) of FIG. 8) and the case where the present method is applied for the refraction correction (part (b) of FIG. 8). When the known method is applied and the sound speed measured within the medium 1 is higher than the sound speed measured within the medium 0, the viewing angle is reduced because the distribution of the virtual reception points is tilted toward the center part as described above. On the other hand, when the present method is applied, the positions of the virtual reception points can be arbitrarily specified. Therefore, it becomes possible to regularly distribute the virtual reception points so that the virtual reception points are not tilted toward the center part. Accordingly, the present method allows for increasing the effective viewing angle and obtaining an increasingly accurate image.

Figure 9:
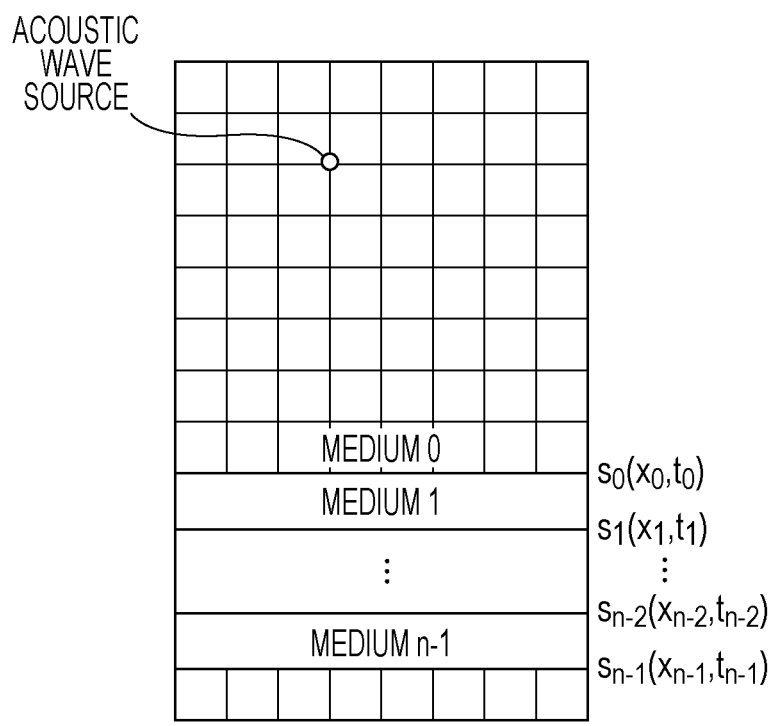
FIG. 9 is a schematic diagram illustrating the case where a plurality of mediums (at least three mediums) having different sound speeds are provided.

FIG. 9 schematically illustrates the case where the present method is applied for a multilayer system. When a structure includes n mediums having different sound speeds, that is, mediums 0 to n−1, signals $s_{n-2}, \ldots, s_1$, and $s_0$ can be obtained in sequence based on transmitted acoustic signal $s_{n-1}$ in accordance with Equation (5). In that case, integrals of the products of an advanced Green's function and the obtained signals are obtained one after another. Further, even though each layer has a plane shape in FIG. 9, each layer may be a curved plane so long as its shape is known.

$$s_0(x_0,t_0) = \int G_A(x_1-x_0,t_1-t_0) \ldots G_A(x_{n-1}-x_{n-2},t_{n-1}-t_{n-2}) s_{n-1}(x_{n-1},t_{n-1})dx_1 dt_1 \ldots dx_{n-1}dt_{n-1} \quad \text{Equation (5)}$$

When the shape and sound speed of each layer are known in the case where a gel used to perform acoustic impedance matching between the subject and the compression plate is provided in the structure, or the case where at least three mediums having different sound speeds, including, for example, a fat layer, a muscle layer, and the compression plate, are provided in the structure, the sequential signals may be mapped in order.

In the above-described embodiments, the virtual reception point is set on the interface between the subject and the compression plate (that is, on the interface between mediums having different sound speeds). However, when the sound speed measured in the subject is considered to be constant, the virtual reception point may be set at any location so long as the location is specified within the subject (that is, the subject side beyond the interface) according to an embodiment of the present invention. In the case of having several different mediums (e.g., FIG. 9) each of which has a different sound speed therein, the virtual reception point may be set on each interface between mediums having different sound speeds and/or in the vicinity of each interface.

Other Embodiments

An embodiment of the present invention is achieved through a simulation, which will be described with reference to FIG. 10. In the above-described embodiment, a calculation is performed in a two-dimensional system having 64×80 pixels. Two layers including a subject part and a compression plate part constitute a structure. The sound speed of the subject part is 1500 m/s, and that of the compression plate part is 2200 m/s. The upper-left corner of the above-described two-dimensional plane is defined as the origin point (0, 0), and the lower-right coordinates that are given before an acoustic wave passes through the compression plate are defined as (63, 63).

Figure 10:
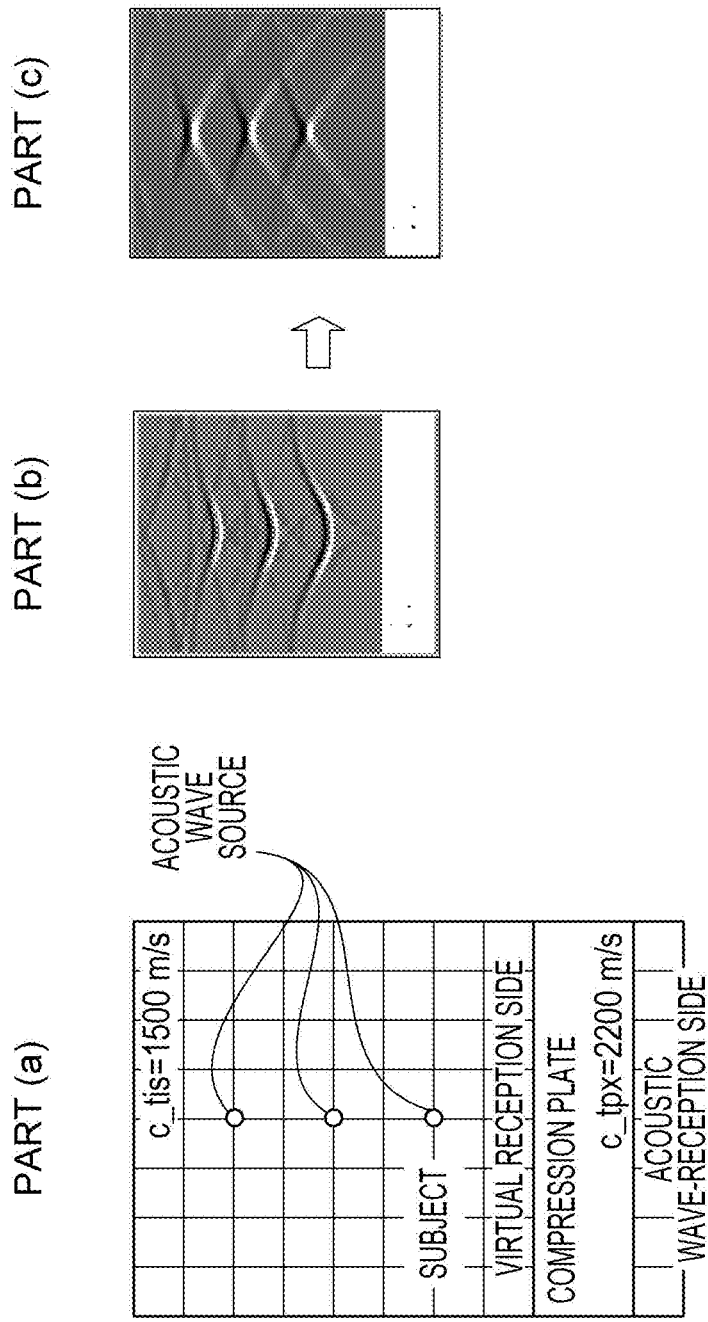
FIG. 10 illustrates advantageous imaging effects obtained with an embodiment of the present invention.

Part (a) of FIG. 10 illustrates an initial-acoustic wave-source distribution provided to generate sample data. An initial-acoustic wave source is set at each of (31, 15), (31, 31), and (31, 47). Further, an acoustic receiver provided to receive the acoustic wave is arranged on the lower side of the compression plate part to receive the acoustic wave that has passed through the compression plate. The number of acoustic wave-receiving elements is 64. The number of time-sampling data is 512.

Part (b) of FIG. 10 illustrates the case where the Fourier domain method is applied and performed based on the above-described sample data without performing the refraction correction. In that case, the Fourier domain method is performed based on the sound speed measured in the subject part with reference to a reception signal obtained at each of acoustic wave-reception points. Part (b) of FIG. 10 illustrates that the lack of the refraction correction causes a significant reduction in the horizontal resolution at the acoustic wave-source estimation time.

Part (c) of FIG. 10 illustrates the case where the Fourier domain method is applied and performed based on the above-described sample data. More specifically, the Fourier domain method is performed based on the sound speed measured within the subject part after generating virtual reception signals that are provided on virtual reception points on regularly-spaced lattice through application of the refraction correction performed according to an embodiment of the present invention. Part (c) of FIG. 10 illustrates that the application of the refraction-correction method performed according to an embodiment of the present invention allows for estimating the acoustic wave sources without significantly reducing the horizontal resolution.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-012192 filed on Jan. 22, 2010, which is hereby incorporated by reference herein in its entirety.

What is claimed is:

1. An image data-generation method, comprising:
using an electronic circuit for generating image data based on a first signal output from an acoustic wave receiver receiving an acoustic wave generated by irradiating a subject with light;
obtaining a second signal based on the first signal; and
generating image data based on the second signal;
wherein the acoustic wave travels from the subject to the acoustic wave receiver via a medium having a sound speed different from a sound speed in the subject,
wherein the second signal is a signal of which an effect of an acoustic wave refraction due to the medium is corrected by performing an integral calculation with an advanced Green's function using the first signal, and
wherein the advanced Green's function represents a time evolution opposite in direction to ordinary time evolution such that the integral calculation allows for calculating a virtual reception signal obtained at a point arbitrarily specified before the acoustic wave passes through the medium.

2. The image data generating method according to claim 1, wherein the second signal corresponds to a receiving signal of the acoustic wave at a virtual reception point that is set within the subject or on an interface between the subject and the medium.

3. The image data generating method according to claim 2, wherein a plurality of the virtual reception points are set at regular intervals.

4. The image data generating method according to claim 1, wherein the image data is generated according to a Fourier domain method based on the second signal.

5. The image data generating method according to claim 1, wherein the image data is generated according to a time domain method based on the second signal.

6. A system comprising:
a light source arranged to irradiate a subject with light;
an acoustic wave receiver arranged to receive an acoustic wave generated in the subject by the light and to convert into a first signal;
a medium having a sound speed different from a sound speed in the subject, the medium being provided between the subject and the acoustic wave receiver; and
a signal processing device including an imaging unit which generates image data,
wherein the signal processing device further includes an obtaining unit configured to obtain a second signal of which an effect of an acoustic wave refraction due to the medium is corrected by performing an integral calculation with an advanced Green's function using the first signal, and
wherein the advanced Green's function represents a time evolution opposite in direction to ordinary time evolution such that the integral calculation allows for calculating a virtual reception signal obtained at a point arbitrarily specified before the acoustic wave passes through the medium, and
wherein the imaging unit generates image data based on the second signal.

7. The system according to claim 6, wherein the obtaining unit obtains the second signal as a receiving signal of the acoustic wave at a virtual reception point that is set within the subject or on an interface between the subject and the medium.

8. The system according to claim 7, wherein the signal processing device sets a plurality of the virtual reception points at regular intervals.

9. The system according to claim 6, wherein the signal processing device generates the image data according to a Fourier domain method based on the second signal.

10. The system according to claim 6, wherein the signal processing device generates the image data according to a time domain method based on the second signal.

11. A system comprising:
a light source arranged to irradiate a subject with light;
an acoustic wave receiver arranged to receive an acoustic wave generated in the subject by the light and to convert the acoustic wave into a first signal;
a medium having a sound speed different from a sound speed in the subject, the medium being arranged between the subject and the acoustic wave receiver; and
a signal processing device including an imaging unit which generates image data,
wherein the signal processing device further includes an obtaining unit configured to obtain a second signal corresponding to an acoustic wave which is before travelling the medium by performing an integral calculation with an advanced Green's function using the first signal, and
wherein the advanced Green's function represents a time evolution opposite in direction to ordinary time evolution such that the integral calculation allows for calculating a virtual reception signal obtained at a point arbitrarily specified before the acoustic wave passes through the medium, and
wherein the imaging unit generates the image data based on the second signal.

12. The system according to claim 11, wherein the obtaining unit obtains the second signal as a receiving signal of the acoustic wave at a virtual reception point that is set within the subject or on an interface between the subject and the medium.

13. The system according to claim 12, wherein the signal processing device sets a plurality of the virtual reception points at regular intervals.

14. The system according to claim 11, wherein the signal processing device generates the image data according to a Fourier domain method based on the second signal.

15. The system according to claim 11, wherein the signal processing device generates the image data according to a time domain method based on the second signal.

16. An image data-generation method, comprising:
using an electronic circuit for generating image data based on a first signal output from an acoustic wave receiver receiving an acoustic wave generated by irradiating a subject with light;
obtaining a second signal based on the first signal;
generating image data based on the second signal;
wherein the acoustic wave travels from the subject to the acoustic wave receiver via a medium having a sound speed different from a sound speed in the subject, and wherein the second signal is obtained by performing an integral calculation with an advanced Green's function on the acoustic wave before travelling the medium, and wherein the advanced Green's function represents a time evolution opposite in direction to ordinary time evolution such that the integral calculation allows for calculating a virtual reception signal obtained at a point arbitrarily specified before the acoustic wave passes through the medium.

17. The image data generating method according to claim 16, wherein the second signal corresponds to a receiving signal of the acoustic wave at a virtual reception point that are set within the subject or on an interface between the subject and the medium.

18. The image data generating method according to claim 17, wherein a plurality of the virtual reception points are set at regular intervals.

19. The image data generating method according to claim 16, wherein image data is generated according to a Fourier domain method based on the second signal.

20. The image data generating method according to claim 16, wherein image data is generated according to a time domain method based on the second signal.

* * * * *